United States Patent
Reddy et al.

(10) Patent No.: US 7,067,675 B2
(45) Date of Patent: Jun. 27, 2006

(54) PROCESS FOR EZETIMIBE INTERMEDIATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 0 days.

(21) Appl. No.: 10/540,093

(22) PCT Filed: Nov. 24, 2003

(86) PCT No.: PCT/IN03/00366

§ 371 (c)(1),
(2), (4) Date: Jun. 20, 2005

(87) PCT Pub. No.: WO2005/049592

PCT Pub. Date: Jun. 2, 2005

(65) Prior Publication Data

US 2006/0069137 A1    Mar. 30, 2006

(51) Int. Cl.
*C07D 263/04*    (2006.01)

(52) U.S. Cl. ..................................... 548/228

(58) Field of Classification Search ................. 548/228
See application file for complete search history.

(56) References Cited

U.S. PATENT DOCUMENTS

| 5,618,707 A | 4/1997 | Homann et al. |
| 5,767,115 A | 6/1998 | Rosenblum et al. |
| 5,886,171 A | 3/1999 | Wu et al. |

FOREIGN PATENT DOCUMENTS

| WO | WO 97/16424 | 5/1997 |
| WO | WO 97/45406 | 12/1997 |
| WO | WO 00/34240 | 6/2000 |

OTHER PUBLICATIONS

J. Med. Chem. 1998, 41(6), 973-980 (Eng).
J. Org. Chem. 1999, 64(10), 3714-18 (Eng).
J. Org. Chem. (1995), 60(25), 5446-8 (Eng).
J. Org. Chem. (1992), 57 (26),7044-52 (Eng).

*Primary Examiner*—Joseph K. McKane
*Assistant Examiner*—Yong Chu
(74) *Attorney, Agent, or Firm*—Caesar, Rivise, Bernstein, Cohen & Pokotilow, Ltd.

(57) ABSTRACT

The invention provides a process for preparing intermediate of ezetimibe, which shows hypocholesterolemic activity. Thus 3-[5-(4-fluorophenyl)-1,5-dioxopentyl]-4-phenyl-2-oxazolidinone is reduced with (−)-DIP chloride to obtain 3-[(5S)-5-(4-fluorophenyl)-5-hydroxy-1-oxopentyl]-4-phenyl-2-oxazolidinone.

13 Claims, No Drawings

PROCESS FOR EZETIMIBE INTERMEDIATE

FIELD OF THE INVENTION

The present invention is related to a simple and economical process for the preparation of ezetimibe intermediate.

BACKGROUND OF THE INVENTION

U.S. Pat. No. 5,767,115 discloses the hypocholesterolemic activity of hydroxy-substituted azetidinones. Processes for preparing these compounds are described in U.S. Pat. No. 5,767,115, WO 97/16424, WO 97/45406, U.S. Pat. No. 5,886,171, WO 00/34240, J. Med. Chem. 1998, 41(6), 973–980 and J. Org. Chem. 1999, 64(10), 3714–18.

WO 00/34240 discloses an improved process for preparing these compounds, in particular ezetimibe, (3R,4S)-1-(4-fluorophenyl)-3-[(3S)-3-(4-fluorophenyl) -3-hydroxypropyl]-4-(4-hydroxyphenyl)-2-azetidinone of formula I.

The reaction sequence of process for preparing ezetimibe is shown in scheme A.

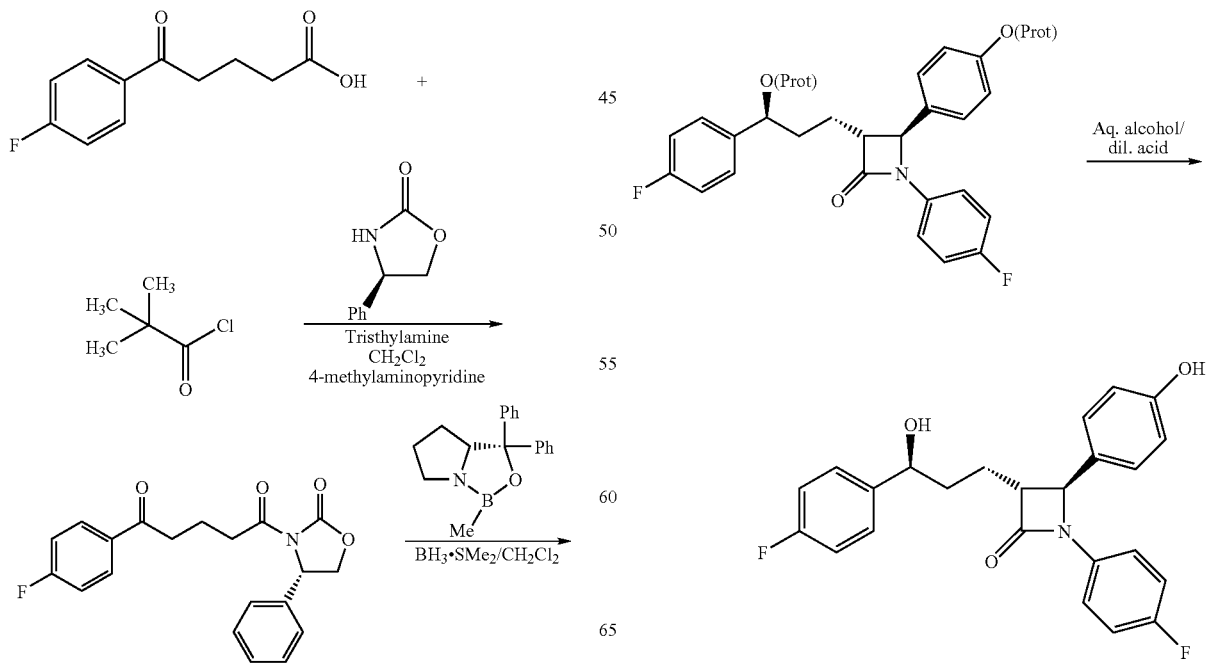

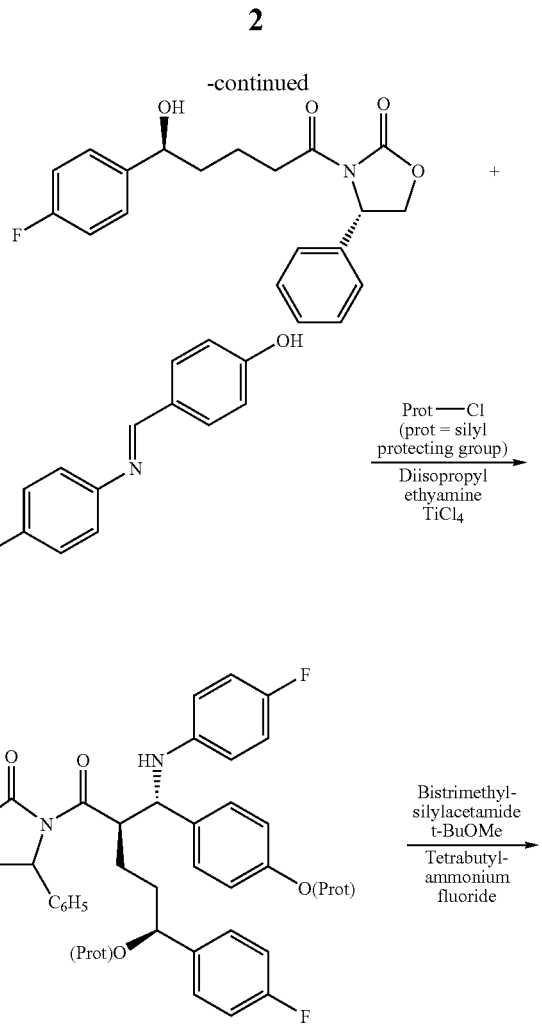

The reduction of the ketone of the formula 3a

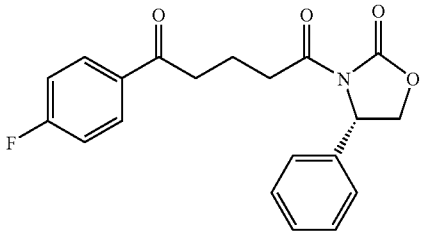

3a to give alcohol of formula 2a

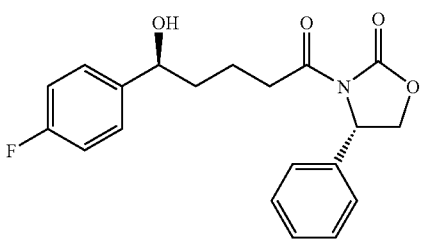

2a involves the use of the reducing agent borane dimethyl sulfide in the presence of the expensive chiral catalyst (R)-tetrahydro-1-methyl-3,3-diphenyl-1H,3H-pyrrolo(1,2-c)(1,3,2) oxaza-borolidine.

U.S. Pat. No. 5,618,707 describes microbial reduction of compound of formula 3a to form the compound of formula 2a. The process requires strict control of cultures and chromatographic separations, which make the process unsuitable for industrial production.

We have discovered that less expensive (−)-DIP chloride ((−)-β-chlorodiisopinocampheylborane) can be used for such asymmetric reductions, thereby avoiding the use of expensive twin reagents i.e. borane dimethyl sulfide and (R)-tetrahydro-1-methyl-3,3-diphenyl-1H,3H-pyrrolo(1,2-c)(1,3,2)oxaza-borolidine, and avoiding the 'difficult to handle' reagents.

Thus the novel process is simple to handle and more economical than the known process.

The term lower alkyl refers to C1–C6 alkyl and the term lower alkoxy refers to C1–C6 alkoxy.

The object of the present invention is to provide a simple, cost effective process for the preparation of the ezetimibe intermediates.

SUMMARY OF THE INVENTION

The present invention provides a process for preparing an alcohol of formula 2

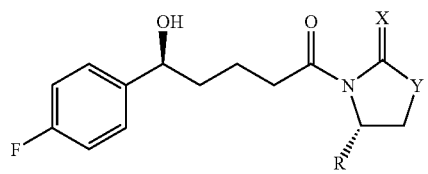

2 wherein X is O or S; Y is O, S or N(lower alkyl); and R is alkyl, unsubstituted or substituted phenyl, unsubstituted or substituted naphthyl or lower alkoxy carbonyl, wherein substituents on phenyl and naphthyl are selected from the group consisting of lower alkyl and phenyl;

which comprises reducing the ketone of formula 3

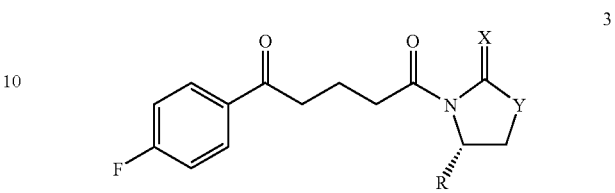

3 wherein X—, Y— and R are as defined above, with (−)-DIP chloride ((−)-β-chlorodiisopinocampheylborane).

The compounds of formula 2 wherein X is O; Y is O; and R is alkyl, unsubstituted or substituted phenyl are the preferred.

The reduction may be carried out in a neutral organic solvent or a combination of the neutral organic solvents. Neutral organic solvent means the solvent that is unreactive in the reduction reaction. The preferable neutral organic solvents are chloroalkanes such as methylene dichloride, chloroform, carbon tetrachloride and ethylene dichloride; carbocyclic aromatics such as toluene and benzene; ethers such as methyl tert-butyl ether, diethylether and isopropyl ether; heterocyclic compound such as tetrahydrofuran; dimethylformamide; dimethylsulfoxide; alkanes such as pentane and hexane; and acetonitrile. More preferable organic solvents are toluene, diethyl ether, isopropyl ether, hexane, methylene dichloride and ethylene dichloride.

Quantity of (−)-DIP chloride used is preferably at least about 0.3 mole, more preferably about 0.5 to 10 mole, most preferably about 0.8 to 5 mole per mole of the keto compound of formula 3.

The preferable reaction temperature is below the boiling temperature of the solvent used, more preferably between about −40° C. and the boiling temperature of the solvent, still more preferably between about −20° C. and 40° C. and most preferably between about −10° C. and 10° C.

DETAILED DESCRIPTION OF THE INVENTION

The compound of the formula 2

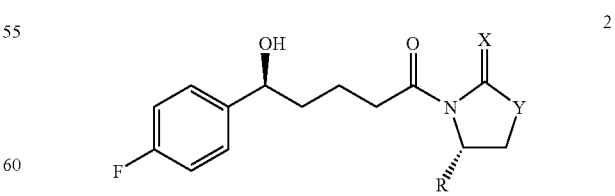

2 is an useful intermediate for the preparation of ezetimibe. The intermediates represented by the formula 2 can be prepared economically in good yields as represented by the scheme B.

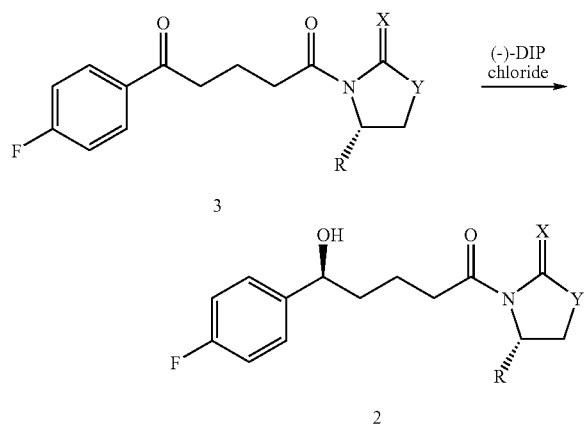

wherein X is O or S; Y is O, S or N(lower alkyl); and R is alkyl, unsubstituted or substituted phenyl, unsubstituted or substituted naphthyl or lower alkoxy carbonyl, wherein substituents on phenyl and naphthyl are selected from the group consisting of lower alkyl and phenyl.

The starting compounds of formula 3 are known or can be obtained from known methods.

The reduction may be carried out in a neutral organic solvent or a combination of the neutral organic solvents. Neutral organic solvent means the solvent that is unreactive in the reduction reaction. The preferable organic solvents are chloroalkanes such as methylene dichloride, chloroform, carbon tetrachloride and ethylene dichloride; carbocyclic aromatics such as toluene and benzene; ethers such as methyl tert-butyl ether, diethylether and isopropyl ether; heterocyclic compound such as tetrahydrofuran; dimethylformamide; dimethylsulfoxide; alkanes such as pentane and hexane; and acetonitrile. More preferable solvents are toluene, diethyl ether, isopropyl ether, hexane, methylene dichloride and ethylene dichloride.

The preferable reaction temperature is below the boiling temperature of the solvent used, more preferably between about −40° C. and the boiling temperature of the solvent, still more preferably between about −20° C. and 40° C. and most preferably between about −10° C. and 10° C.

Quantity of (−)-DIP chloride used is preferably at least about 0.3 mole, more preferably about 0.5 to 10 mole, most preferably about 0.8 to 5 mole per mole of the keto compound of formula 3.

Yield of the hydroxy compound of formula 2 is usually above 80%, typically between 90% to 100%.

The compounds of formula 2 wherein X is O; Y is O; and R is alkyl, unsubstituted or substituted phenyl are the preferred.

Preferable conditions for obtaining a hydroxy compound of formula 2 from the corresponding keto compound of formula is that the keto compound of the formula 3 is mixed with a neutral solvent, reduced with (−)-DIP chloride at a temperature between −40° C. and the boiling temperature of the solvent, more preferably between about −20° C. and 40° C. and most preferably between about −10° C. and 10° C.

The reaction mass may be subjected to usual work up. The reaction mass may be used directly in the next step to produce finally ezetimibe, or the hydroxy compound may be isolated and used in the next step.

The invention will now be further described by the following examples, which are illustrative rather than limiting.

EXAMPLE 1

3-[5-(4-fluorophenyl)-1,5-dioxopentyl]-4-phenyl-2-oxazolidinone (100 gm) is dissolved in toluene (750 ml), the mixture of (−)-β-chlorodiisopinocampheylborane ((−)-DIP chloride) in heptane (545 ml, 1.5M) and toluene (750 ml) is added at 0° C. to 5° C. for 1 hour. The reaction mixture is stirred for 15 hours at 25° C. to 30° C. and 340 ml of 10% sodium chloride is then added at the same temperature. The layers are separated and the organic layer is washed with 5% sodium bicarbonate (300 ml), 1N sulfuric acid (300 ml), and 10% sodium chloride (300 ml). Then the organic layer is dried on sodium sulfate to give 3-[(5S)-5-(4-fluorophenyl)-5-hydroxy-1-oxopentyl]-4-phenyl-2-oxazolidinone in 96% yield.

EXAMPLE 2

The organic layer of 3-[(5S)-5-(4-fluorophenyl)-5-hydroxy-1-oxopentyl]-4-phenyl-2-oxazolidinone from example 1 is mixed with 4-fluoro-N-(4-hydroxyphenyl)methylene-benzenamine (121 gm) and cooled to −10° C. Then diisopropylethylamine (260 ml) is added to the reaction mixture for 45 minutes at −10° C. to −15° C., trimethylsilylchloride (135 ml) is added and stirred for 1 hour at −20° C. to −25° C. The reaction mixture is cooled to −30° C., TiCl$_4$ (35 ml) is slowly added to the reaction mixture at −30° C. to −35° C. and stirred for 3 hours at the same temperature. 5% Aq. tartaric acid solution (1700 ml) is added to the reaction mixture at 0° C., stirred for 1 hour and allowed the temperature to rise to 25° C. Then 20% Aq. NaHSO$_3$ (350 ml) solution and stirred for 2 hours at 25° C. to 30° C. The organic layer is separated and washed with 1000 ml water, concentrated to 250 ml volume and added 100 ml bistrimethylsilylacetamide. Then the reaction mixture is heated to reflux for 30 minutes. The organic layer is concentrated to remove methylene dichloride, crystallized from the mixture of ethyl acetate (250 ml) and n-heptane (250 ml), and filtered and dried to give 135 gm of compound 4 (prot=trimethylsilyl).

We claim:

1. A process for the preparation of an alcohol of formula 2:

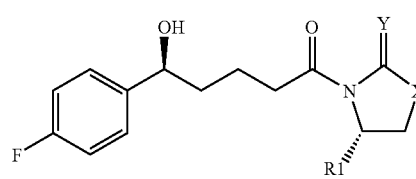

wherein X is O or S; Y is O, S or N(lower alkyl); and R$^1$ is alkyl, unsubstituted or substituted phenyl, unsubstituted or substituted naphthyl or lower alkoxy carbonyl, wherein substituents on phenyl and naphthyl are selected from the group consisting of lower alkyl and phenyl;

which comprises reducing the ketone of formula 3:

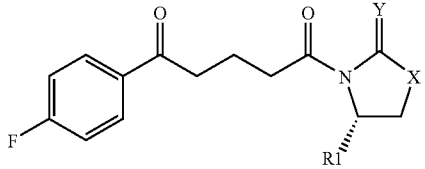

wherein X—, Y— and R1 are as defined above, with (−)-DIP chloride ((−)-β-chlorodiisopinocampheylborane).

2. A process according to claim 1, wherein X is O; Y is O; and R is alkyl, unsubstituted or substituted phenyl.

3. A process according to claim 1, wherein the compound of the formula 2 is 3-[(5S)-5-(4-fluorophenyl)-5-hydroxy-1-oxopentyl]-4-phenyl-2-oxazolidinone.

4. A process according to claim 1, wherein the reduction is carried out in a neutral organic solvent or a combination of the organic solvents.

5. A process according to claim 4, wherein the organic solvent is selected from the group consisting of chloroalkanes such as methylene dichloride, chloroform, carbon tetrachloride and ethylene dichloride; carbocyclic aromatics such as toluene and benzene; ethers such as methyl tert-butyl ether, diethyl ether and isopropyl ether; heterocyclic compound such as tetrahydrofuran; dimethylformamide; dimethylsulfoxide; alkanes such as pentane and hexane; and acetonitrile.

6. A process according to claim 5, wherein the organic solvent is selected from the group consisting of methylene dichloride, chloroform, carbon tetrachloride, ethylene dichloride, toluene, benzene, methyl tert-butyl ether, diethyl ether, isopropyl ether, tetrahydrofuran, dimethylformamide, dimethylsulfoxide, pentane, hexane and acetonitrile.

7. A process according to claim 6, wherein the organic solvent is selected from toluene, diethyl ether, isopropyl ether, hexane, methylene dichloride and ethylene dichloride.

8. A process according to claim 1, wherein the reaction is carried out below the boiling temperature of the solvent.

9. A process according to claim 8, wherein the reaction is carried out between about −20° C. and 40° C.

10. A process according to claim 9, wherein the reaction is carried out between about −10° C. and 10° C.

11. A process according to claim 1, wherein at least about 0.3 moles of (−)-DIP chloride per mole of the keto compound of formula 3 is used.

12. A process according to claim 11, wherein about 0.5 to 10 moles of (−)-DIP chloride per mole of the keto compound of formula 3 is used.

13. A process according to claim 12, wherein about 0.8 to 5 moles of (−)-DIP chloride per mole of the keto compound of formula 3 is used.

* * * * *